(12) United States Patent
Wei et al.

(10) Patent No.: US 7,615,636 B2
(45) Date of Patent: Nov. 10, 2009

(54) RUTHENIUM COMPLEXES WITH TRIDENTATE HETEROCYCLIC LIGAND AND DYE-SENSITIZED SOLAR CELLS USING THE SAME

(75) Inventors: Ching-Yen Wei, Taipei (TW); Chao-Ining Yu, Kaohsiung County (TW); Fu-Ching Tung, Hsinchu (TW); Yun Chi, Hsinchu (TW); Hsing-Yi Chen, Chiayi County (TW); I-Hui Lin, Yilan County (TW)

(73) Assignee: Industrial Technology Research Institute, Hsinchu (TW)

( * ) Notice: Subject to any disclaimer, the term of this patent is extended or adjusted under 35 U.S.C. 154(b) by 30 days.

(21) Appl. No.: 11/939,559

(22) Filed: Nov. 14, 2007

(65) Prior Publication Data
US 2008/0114174 A1    May 15, 2008

(30) Foreign Application Priority Data
Nov. 14, 2006    (TW) ................................ 95142037 A

(51) Int. Cl.
*C07F 15/00* (2006.01)
*H01L 31/00* (2006.01)

(52) U.S. Cl. .......................... 546/2; 136/252; 136/263; 556/137

(58) Field of Classification Search ..................... 546/2; 556/137; 136/252, 263
See application file for complete search history.

(56) References Cited

U.S. PATENT DOCUMENTS 6,639,073 B2    10/2003    Islam et al.

FOREIGN PATENT DOCUMENTS

WO          98/50393          11/1998

OTHER PUBLICATIONS

Article titled "Engineering of Efficient Panchromatic Sensitizers for Nanocrystalline TiO2-Based Solar Cells" jointly authored by Nazeeruddin et al., J. Am. Chem. Soc. 2001, 123, pp. 1613-1624.
Article titled "Conversion of Light to Electricity by cis-X2Bis(2,2'-bipyridyl-4,4'-dicarboxylate)ruthenium(II) Charge-Transfer Sensitizers (X=Cl−, I−, CN−, and SCN−) on Nanocrystalline TiO2 Electrodes" jointly authored by Nazeeruddin et al., , J. Am. Chem. Soc. 1993, 115, pp. 6382-6390.

*Primary Examiner*—Charanjit S Aulakh
(74) *Attorney, Agent, or Firm*—Jianq Chyun IP Office

(57) ABSTRACT

A ruthenium complex is provided. The ruthenium complex is represented by the following Formula (I):

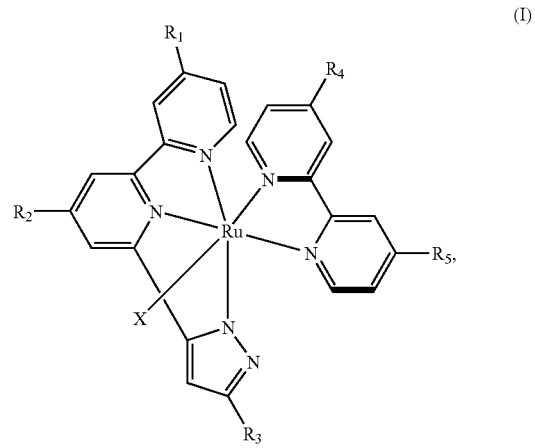

in which, X is a monodentate anion ligand, $R_1$, $R_2$, $R_4$ and $R_5$ are the same or different substituents and represent alkyl, alkoxy, aminoalkyl, haloalkanes or substituted phenyl group, carboxylic acid group or acid radical salt thereof, sulfonic acid group or acid radical salt thereof, phosphoric acid group or acid radical salt thereof or hydrogen atom. $R_3$ represents perhalogenated alkyl group, alkoxy, alkyl, amino, halogens, or hydrogen atom. The ruthenium complexes are suitable for being used as dye-sensitizers for fabricating dye-sensitized solar cells.

21 Claims, 1 Drawing Sheet

RUTHENIUM COMPLEXES WITH TRIDENTATE HETEROCYCLIC LIGAND AND DYE-SENSITIZED SOLAR CELLS USING THE SAME

CROSS-REFERENCE TO RELATED APPLICATION

This application claims the priority benefit of Taiwan application serial no. 95142037, filed Nov. 14, 2006. All disclosure of the Taiwan application is incorporated herein by reference.

BACKGROUND OF THE INVENTION

1. Field of the Invention

The present invention relates to a dye-sensitizer made of a novel heterocyclic tridentate ligand and dye-sensitized solar cells using the same.

2. Description of Related Art

Since Michael Grätzel proposed to fabricate a dye-sensitized solar cell (DSSC) by using a porous $TiO_2$ thin film as a semiconductor electrode, and taking an organic metal compound as a photosensitive dye, together with a suitable redox electrolyte, this kind of solar cells has become one of the most promising third generation solar cells following silicon p-n junction solar cells. As the property of the dye for the dye-sensitized solar cell may directly affect the photoelectric conversion efficiency and commercial potentials of the solar cells, the photosensitive dye has become one of the key issues when researching this type of cells.

In the current development, a desirable photoactive dye is $ML_2(X)_2$, in which M represents ruthenium (Ru), $L_2$ represents 4,4'-dicarboxyl-2,2'-bipyridine, and X represents halogen, cyano, thiocyanate, acetylacetonato, thiocarbamate, water, and the like. In this series of dyes, the "N3 dye", in which X is thiocyanate, has the most desirable properties and with structure depicted below. However, as the matching degree between the absorption spectrum range for the N3 dyes and the solar spectrum is not desirable, and the N3 dye has a poor response to the spectrum of over 600 nm, so that this part of the solar energy cannot be effectively used.

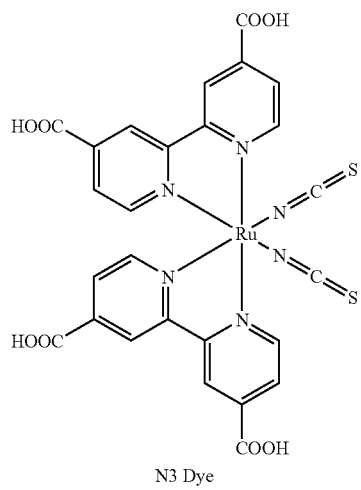

N3 Dye

Additionally, there is another photoactive dye called "black dye" [having a structural formula of $RuL_3(SCN)_3$ (L=tripyridyltricarboxylate)], which can overcome the disadvantages of the N3 dye, and has a structure as follows.

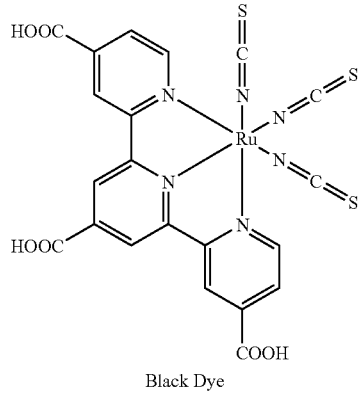

Black Dye

Although the above two photoactive dyes have relatively high photoelectric conversion efficiency in the visible region and the "black dye" still has spectrum response at 920 nm, the "black dye" was not extensively employed as the photosensitive dye due to the tedious synthetic procedures and lower reaction yield.

SUMMARY OF THE INVENTION

Accordingly, the present invention is directed to a novel ruthenium (Ru) complex, which may be used as a dye-sensitizer to enlarge an absorption region for solar spectrum.

The present invention is further directed to a dye-sensitized solar cell device, which has a high efficiency.

The present invention provides a ruthenium (Ru) complex having a formula of $RuL_1L_2X$, and the structural formula is represented as Formula (I) listed below:

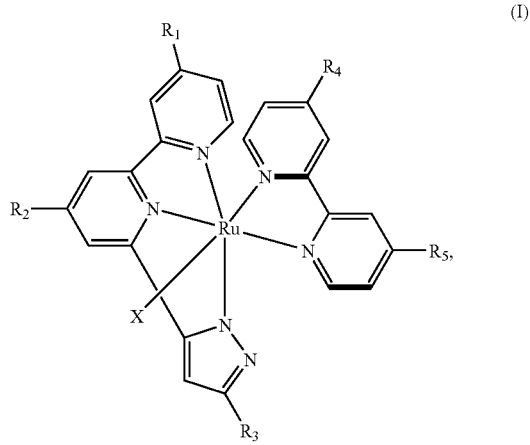

(I)

in which $L_1$ represents a heterocyclic tridentate ligand with a structural formula (II):

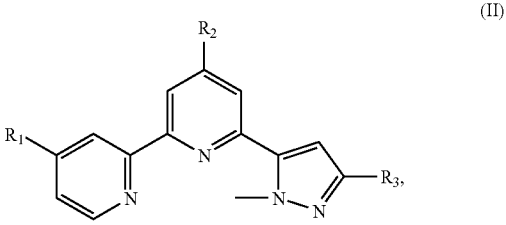

(II)

and L₂ represents a bipyridine ligand derivative with a structural formula (III):

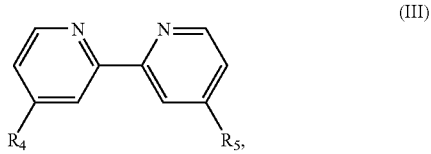

(III)

in which $R_1$, $R_2$, $R_4$ and $R_5$ are the same or different substituents and represent alkyl, alkoxy, aminoalkyl, haloalkanes or substituted phenyl group, carboxylic acid group or acid radical salt thereof, sulfonic acid group or acid radical salt thereof, phosphoric acid group or acid radical salt thereof or hydrogen atom; and $R_3$ represents perhalogenated alkyl group, alkoxy, alkyl, amino, halogens, or hydrogen atom; and X is a monodentate anion ligand.

The present invention further provides a dye-sensitized solar cell device, at least includes a cathodic electrode, an anodic electrode, and an electrolyte fluid. The first electrode includes a transparent conductive substrate and a porous $TiO_2$ thin film. The porous $TiO_2$ thin film is formed on a surface of the transparent conductive substrate and carries the ruthenium complex as a dye-sensitizer. The electrolyte fluid is located between the second electrode and the surface of the transparent conductive substrate having the porous $TiO_2$ thin film.

As the present invention provides a easily-synthesized novel heterocyclic tridentate system as a donor ligand system, the highest occupied molecular orbital (HOMO) energy level for the dye-sensitizer can be effectively controlled, and thus reducing the band gap and promoting the metal-to-ligand charge transfer (MLCT) transition, thereby enhancing the charge separation efficiency. Furthermore, the scope for the dye sensitization is extended towards long wavelength, and accordingly, the absorption region for the solar spectrum is increased. Meanwhile, high-efficiency solar cell devices can be obtained through using the photosensitive dye of the present invention.

In order to make the aforementioned and other objects, features and advantages of the present invention and comprehensible embodiments accompanied with figures are described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, explain the principles of the invention.

DESCRIPTION OF EMBODIMENTS

Figure 1:
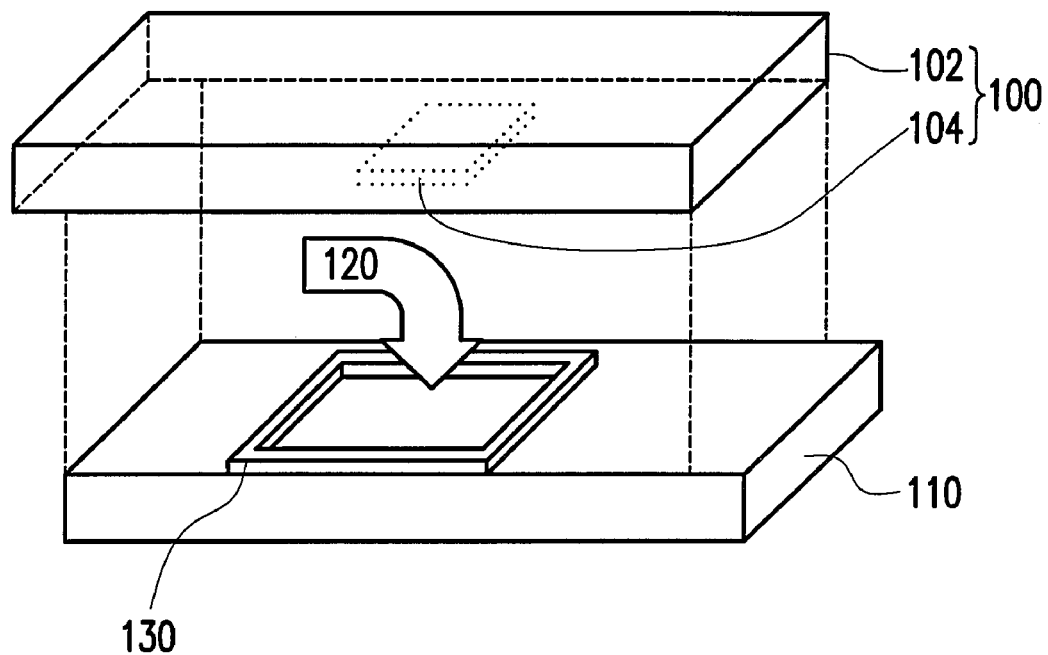
FIG. 1 is an exploded perspective view of an opened dye-sensitized solar cell device according to a sixth embodiment of the present invention.

The heterocyclic tridentate ligand of the ruthenium complex in the present invention has a structural formula (II):

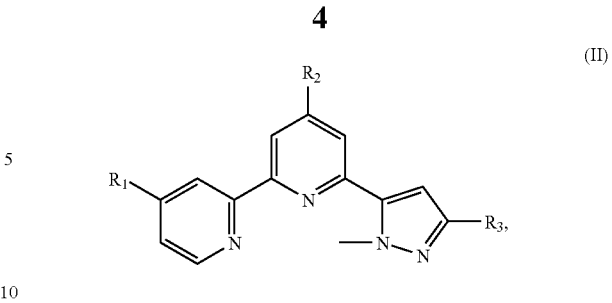

(II)

in which $R_1$ and $R_2$ are the same or different substituents and represent alkyl, alkoxy, aminoalkyl, haloalkanes or substituted phenyl group, carboxylic acid group or acid radical salt thereof, sulfonic acid group or acid radical salt thereof or hydrogen atom. $R_3$ represents perhalogenated alkyl group, alkoxy, alkyl, amino, halogens, or hydrogen atom.

The following embodiments are the embodiments for synthesizing the heterocyclic tridentate ligand with the ruthenium complex, which are intended to illustrate the practical applications of the present invention in detail, but not to limit the application scope of the present invention.

First Embodiment

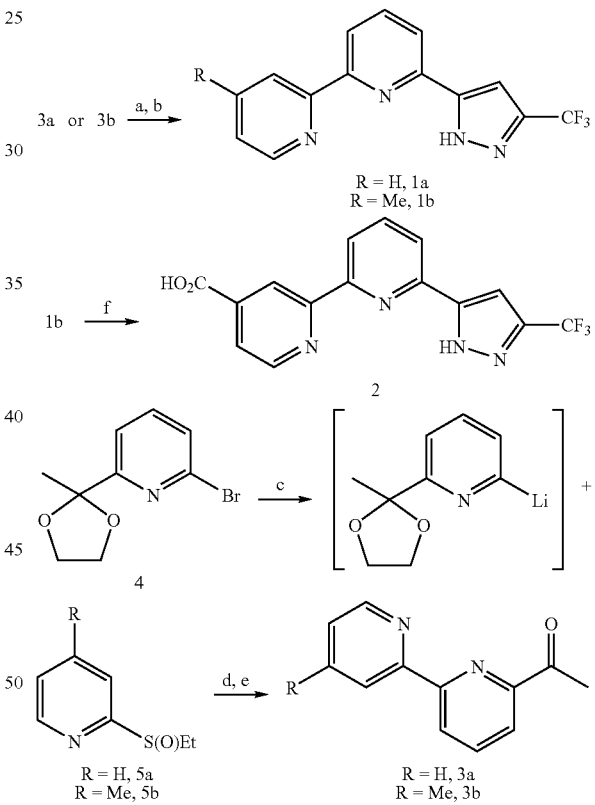

Key Steps:
a) $CF_3CO_2Et$, NaOEt, THF, reflux.
b) $N_2H_4$, EtOH, reflux.
c) η-BuLi, $Et_2O$, −78° C.
d) THF, 25° C.
e) 2M HCl, 60° C., 2 hr.
f) $K_2Cr_2O_7/H_2SO_4$.

NaOEt (1.04 g, 15.6 mmol) was added into 50 mL of THF solvent and they were stirred at 0° C.; next, 6-acetyl-2,2'-bipyridine (3a, 2.0 g, 10.1 mmol) dissolved in 20 mL of THF was added into the reactant; and finally, ethyl trifluoroacetate (1.5 mL, 11.4 mmol) was added. The mixture was heated to reflux and reacted for 12 hr, and then, 2M hydrochloric acid was added till the pH value of the solution reached 8-9. The mixture was extracted with 100 mL of ethyl acetate twice, after combining the organic layer, washed with deionized water and dried with magnesium sulfate. After vacuum concentration, a diketone (2.7 g) was obtained.

Without any purification step, the diketone was dissolved in 60 mL of ethanol, and then hydrazine monohydrate (98%, 4.2 mL, 86.0 mmol) was added. The mixture was heated to reflux and reacted for 12 hr, and the solvent was vacuum-concentrated. The residue was added into 100 mL of dichloromethane and dissolved, and then washed with water. Magnesium sulfate was added to remove water. After vacuum concentration, the residue was purified by means of liquid chromatography through using a silica gel column, and the eluent is ethyl acetate and n-hexane with a ratio of 1:1. Finally, 1.2 g of white solid was obtained, and the yield was 40%. Experimental method of 1b is similar to that of 1a.

Second Embodiment

The solid 1b (0.7 g, 2.30 mmol) was slowly added into sulfuric acid (98%, 16 mL) while stirring severely; next, 1.6 g of potassium dichromate was slowly added, and the temperature was maintained at 80° C., the mixture was stirred till the temperature returned to the room temperature. The dark green mixture was poured into 100 mL of ice-water solutions, and placed overnight at 5° C. The precipitate was filtered and washed with water, and added into 16 mL, 50% of aqueous solution of nitric acid, and then heated to reflux for 5 hr. After cooling to the room temperature, the mixture was poured into 100 mL of ice-water solutions, and placed overnight at 5° C. The precipitate was filtered and then washed with 10 mL of water twice and washed with 5 mL of diethyl ether twice, to get 0.51 g of white solid product 2.

After executing the above procedures, the heterocyclic tridentate ligand of the present invention was obtained. Thereafter, the heterocyclic tridentate ligand is taken as a donor ligand system to prepare the ruthenium (Ru) complex of the present invention, which may be applied to prepare a novel dye-sensitizer.

The ruthenium (Ru) complex of the present invention has the chemical formula of $RuL_1L_2X$ and the structural formula of Formula (I):

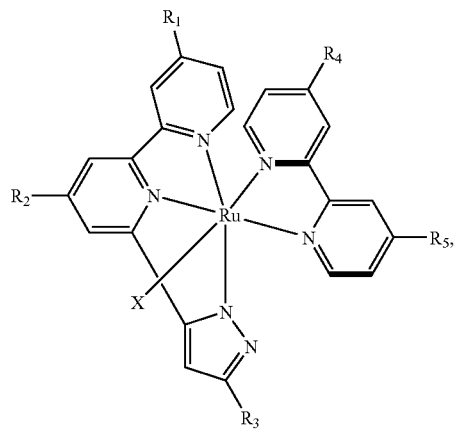

(I)

in which $R_1$, $R_2$, $R_4$, and $R_5$ are the same or different substituents and represent alkyl, alkoxy, aminoalkyl, haloalkanes or substituted phenyl group, carboxylic acid group or acid radical salt thereof, sulfonic acid group or acid radical salt thereof, phosphoric acid group or acid radical salt thereof, or hydrogen atom; $R_3$ represents an electron withdrawing group, such as perhalogenated alkyl group, alkoxy, alkyl, amino, halogens, or hydrogen atom; and X represent a monodentate anion ligand. Furthermore, $R_1$ represents hydrogen or alkyl, and preferably $C_{1-30}$ alkyl, or $R_1$ represents COOH or acid radical salt thereof, $R_2$ represents hydrogen or alkyl, and preferably $C_{1-30}$ alkyl, or $R_2$ represents COOH or acid radical salt thereof; and $R_3$ represents alkyl, perfluorinated alkyl group or alkoxy, and preferably $C_{1-30}$ alkyl, $C_{1-30}$ alkoxy or $CF_3$.

Additionally, $L_1$ is a bipyridine derivative based on the heterocyclic tridentate ligand and has a structure of Formula (II):

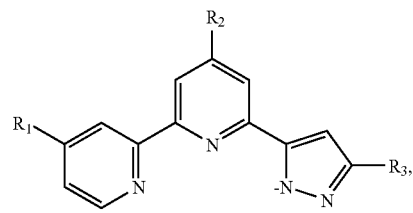

(II)

in which $R_1$, $R_2$, and $R_3$ have the same definitions as that in Formula (I).

The second ligand $L_2$ is a bidentate group, for example, 2,2'-bipyridine, and has a structural formula (III):

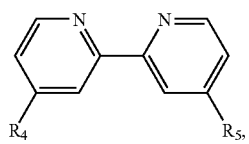

(III)

in which $R_4$ and $R_5$ have the same definitions as that of $R_4$ and $R_5$ of the complex (I). $R_4$ preferably represents COOH. Furthermore, $R_5$ preferably represents COOH.

The ligands $L_1$ and $L_2$ have at least one functional group selected from an organic acid group or acid radical salt thereof, such as carboxylic acid group or acid radical salt thereof, sulfonic acid group or acid radical salt thereof, and phosphoric acid group of acid radical salt thereof.

X is a monodentate ligand, for example, halogen, such as chlorine atom (Cl), halogen ions, halogen cyanide ions, sulfur cyanide ion, sulfite ion, or thiosulfate, and preferably isothiocyanate (NCS).

$L_1$ of the ruthenium complex has, for example, a structural formula (IV):

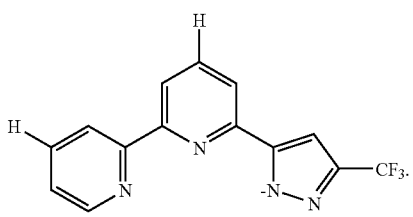

(IV)

Furthermore, $L_2$ of the ruthenium complex has, for example, a structural formula (V):

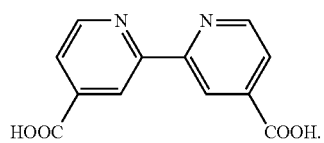

(V)

The third embodiment involves a synthesis step (S1) of the ruthenium complex of the present invention.

Third Embodiment

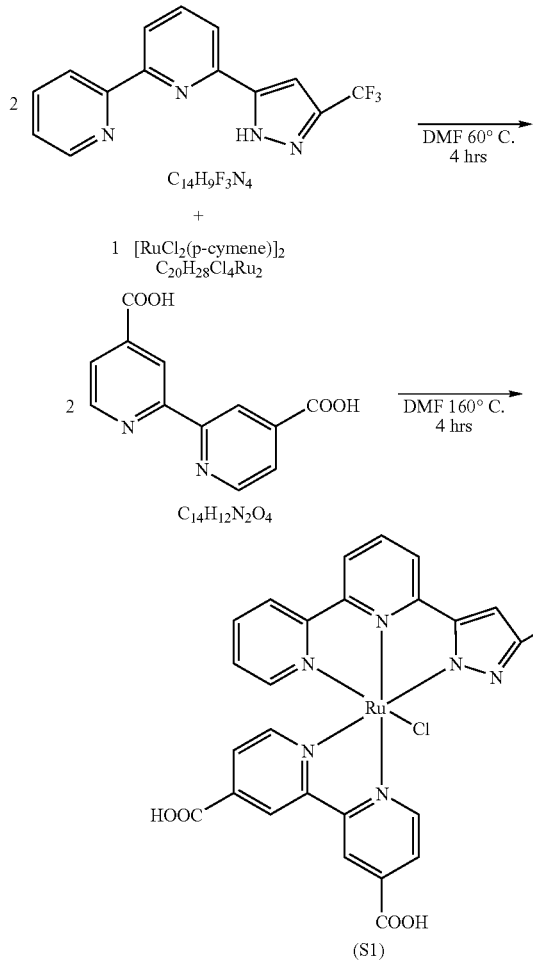

Synthesis of Compound S1
[Ru(bpypz)(H$_2$-dcbpy)Cl]

The ligand 1a and 0.20 g (0.327 mmol) of [RuCl$_2$(p-cymene)]$_2$ were added into a reaction bottle. Under the nitrogen atmosphere, 15 mL of N, N-dimethylformamide was added and reacted at 60° C. for 4 hr. Next, 0.16 g (0.655 mmol) of the ligand [2,2']bipyridinyl-4,4'-dicarboxylic acid (H$_2$-dcbpy) was added into the reaction bottle, and reacted at 150° C. for 4 hr under dimethylformamide (DMF) atmosphere. After the reaction, the DMF was vacuumed, a small amount of DMF (1-2 mL) was added, and then acetonitrile CH$_3$CN (5-7 mL) was added. The mixture was ultrasonic-vibrated for 20 min, and centrifuged to get a solid. The solid was washed with acetonitrile, to get 0.2 g of a first-step compound S1 [Ru(bpypz)(H$_2$-dcbpy)Cl] (46% yield). In the final product, R$_2$ and R$_1$ of the heterocyclic tridentate ligand L$_1$ are hydrogen atoms, R$_3$ is CF$_3$, the bidentate ligand L$_2$ has the structure of Formula (IV), and X is Cl.

Furthermore, the ruthenium complex obtained in Step (S1) may be used to perform the following Step (S2), to get another ruthenium complex of the present invention.

Fourth Embodiment

Synthesis of Compound S2

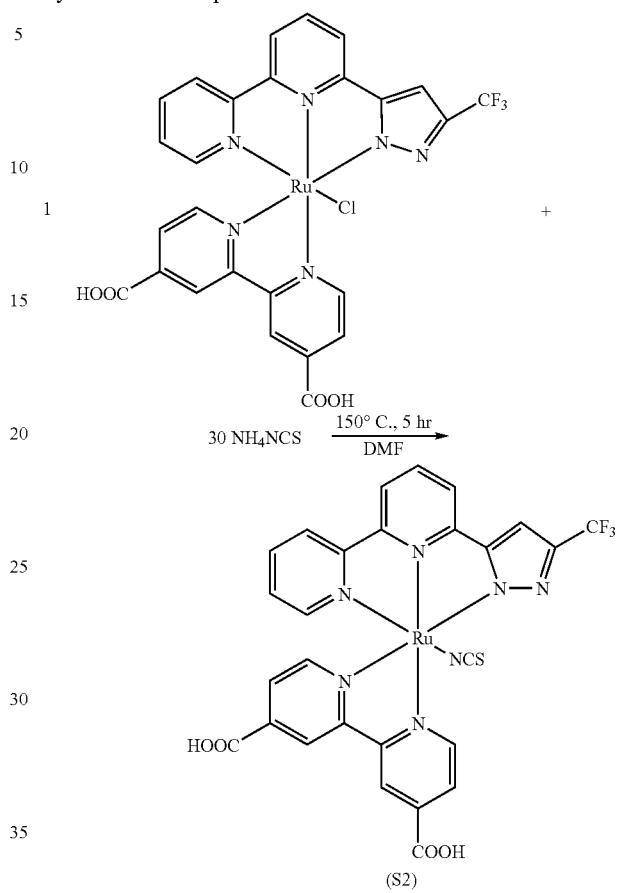

0.10 g (0.150 mmol) of compound 7 and 0.34 g (4.5 mmol) of NH$_4$NCS were added in a reaction bottle, and 15 mL of DMF was added and reacted at 140° C. for 5 hr. Next, DMF was vacuumed, and deionized water (5-7 mL) was added. The mixture was centrifuged to get a solid. Then, the solid was washed with CH$_3$CN to get 0.08 g of a second-step product Ru(bpypzCF$_3$)(H$_2$-dcbpy)NCS (77% yield). R$_2$ and R$_1$ of the heterocyclic tridentate ligand L$_1$ are hydrogen atoms, R$_3$ is CF$_3$, the bidentate ligand L$_2$ has a structure of Formula (IV), and X is NCS.

When the ruthenium complex of the present invention is applied in a dye-sensitized solar cell device as a dye-sensitizer, as the ruthenium complex of the present invention can effectively control the HOMO energy level of the dye-sensitizer, thus reducing the band gap and promoting the metal-to-ligand charge transfer (MLCT) effect, thereby enhancing the charge separation efficiency. Furthermore, the scope for the dye sensitization is extended towards long wavelength, such that the absorption region for the solar spectrum is increased, and thus a high-efficient dye-sensitized solar cell device can be fabricated. Therefore, a solar cell device of about 25 mm$^2$ fabricated by the dye can achieve a photoelectric conversion efficiency of greater than or equal to 5% when being irradiated by a light source of AM 1.5, 100 mw.

Fifth Embodiment

Fabrication of the first electrode (without the dye) of the dye-sensitized solar cell device:

First, it should be noted that, "first" and "second" mentioned in the present invention are intended to make the description of the present invention simple and be easily understood, for example, a first electrode and a second electrode, which do not have any difference in sequence. The transparent conductive substrate of the first electrode is FTO glass (F dopes $SnO_2$ glass) available from Japan Sheet Glass, which is about 1.1 mm thick (Custom made), 7-9 Ω/□.

Furthermore, Ti Nanooxide-D available from Solarinix Company can be directly used; alternatively, Solarinix Ti Nanooxide-D and PEG 20000 available from Wako Company are mixed at a weight ratio of 30:1 to serve as the $TiO_2$ raw material, and the mixing time is 90 min.

Fabricating Process:

1. A $TiO_2$ paste was uniformly mixed for 24 hr.
2. An FTO glass was cut into a size of 2 cm×12.5 cm, placed in a measuring cylinder and ultrasonic-vibrated for 5 min, washed with water, and then washed with deionized water, and then vibrated and washed with acetone for 10 min.
3. An FTO glass was placed on a suction plate with two ends bonded to the suction plate tightly by an adhesive tape, and other air holes were sealed by an adhesive tape; next, the FTO glass was vacuumed; and then, the applicator adjusted the thickness to 4 MIL (1 MIL=25.4 µm); thereafter, 0.0186 g of $TiO_2$ paste was placed at one end of the FTO glass and then coated on the FTO glass at an uniform rate by the applicator to reach a thickness of about 100 µm.
4. The $TiO_2$ paste was dried at 40° C. for 15 min; next, the whole glass substrate was sintered at 550° C., and then placed on a heating plate at 150° C. to be cooled down to room temperature slowly, so as to get the first electrode of the fifth embodiment.

Sixth Embodiment

Fabrication of an Opened Dye-sensitized Solar Cell Device:

Various types of dye-sensitized solar cell devices may be fabricated through using the substrate of the fifth embodiment, one of them is an opened dye-sensitized solar cell device (opened DSSC), and the fabricating process thereof is described as follows.

1. The FTO glass coated with a $TiO_2$ paste (also called $TiO_2$/FTO glass) was cut into 2 cm×1.5 cm, 25-30 $mm^2$ of $TiO_2$ at the center was retained, and the unwanted $TiO_2$ was removed, and the retained $TiO_2$ may be in a circular, quadrate, or polygonal shape.
2. The $TiO_2$/FTO glass was sintered at 55° C. for 10 min and then cooled down slowly.
3. Formulation of the Dye Solution: 0.036 g of S2 dye was dissolved in 25 mL of ethanol; next, 25 mL of t-BuOH and 50 mL of acetonitrile were added, to get a dye solution of 3 mM.
4. Fabrication of the First Electrode (also called dye/$TiO_2$/FTO electrode): The cooled $TiO_2$/FTO glass was placed in a culture dish containing the dye solution (2 mL for each dish) and immersed for 24 hr; next, the dye/$TiO_2$/FTO electrode was rinsed with ethanol to remove the unabsorbed dye; and then, the electrode was dried at 80° C. on the heating plate.
5. Preparation of Electrolyte: the concentration for each substance is listed as follows: 1,2-dimethyl-3-propylimidazolium iodide (DMPImI): 0.6M; LiI: 0.1M; tert-butyl pyridine (TBP): 0.5M; $I_2$: 0.05M in 5 ml methoxyacetonitrile.
6. Fabrication of the Second Electrode: First, a Pt electrode was used as a substrate, in which the Pt electrode is, for example, a common glass doped with Pt and an alloy thereof, such as Pt—Cr (from Peccell); next, a sealant (Surly available from DuPont) was cut into frame capable of enclosing the $TiO_2$ area, and placed on the Pt electrode; and then, the sealant was heated at 110° C. on a heating plate and thus being bonded, so as to complete the fabrication of the second electrode.
7. Thereafter, the first electrode fabricated in the Step 4 was placed in another culture dish containing acetonitrile, washed and wiped; then, 150 µL of the formulated electrolyte fluid was sucked and placed on the second electrode.
8. Assembly of the Opened Dye-sensitized Solar Cell: The second electrode already with the electrolyte fluid dropped thereon was covered on the first electrode in a staggered manner, so as to complete the assembly.

FIG. 1 is an exploded perspective view of an opened dye-sensitized solar cell device according to the sixth embodiment of the present invention.

Referring to FIG. 1, the dye-sensitized solar cell device is formed by a first electrode 100, a second electrode 110, and an electrolyte fluid 120. The first electrode 100 includes a transparent conductive substrate 102 (such as an FTO glass) and a porous $TiO_2$ thin film 104 formed on the surface of the transparent conductive substrate 102. The porous $TiO_2$ thin film 104 carries the ruthenium complex prepared in Step (S2) as a dye-sensitizer. The second electrode 110 is, for example, a Pt electrode formed by a common glass doped with Pt and an alloy thereof, such as, Pt—Cr. The electrolyte fluid 120 is located between the second electrode 110 and the surface of the transparent conductive substrate 102 having the porous $TiO_2$ thin film 104, which is preferably within the area surrounded by the sealant 130.

Seventh Embodiment

Fabrication of a Closed Dye-sensitized Solar Cell Device:

A closed dye-sensitized solar cell device (closed DSSC) can also be fabricated through using the substrate of the fifth embodiment, in which the fabricating process is listed as follows.

Figure 2:
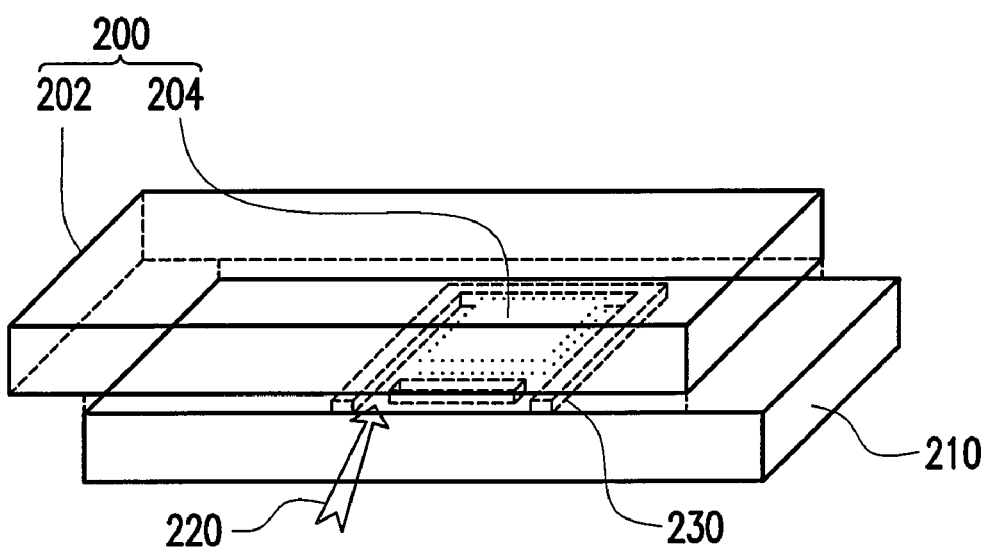
FIG. 2 is an exploded perspective view of a closed dye-sensitized solar cell device according to a seventh embodiment of the present invention.

1. Fabrication of the Second Electrode (Pt electrode): The steps here were substantially the same as those steps for fabricating the opened dye-sensitized solar cell device of the sixth embodiment, but the difference there-between merely lied in that the sealant did not form a closed pattern, but a shape with two pores.
2. After being washed, the first electrode (dye/$TiO_2$/FTO electrode) was placed on the second electrode in a staggered manner, and then heated at 110° C. to make the two electrodes be bonded completely.
3. The electrolyte fluid was slowly injected by a microsyringe via a pore left on the sealant, so as to be adsorbed between the two electrodes due to capillarity, and the unwanted electrolyte fluid was wiped off. Till this step, an exploded perspective view of a closed dye-sensitized solar cell device is shown in FIG. 2. The closed dye-sensitized solar cell device includes a first electrode 200, a second electrode 210, and an electrolyte fluid 220. Similarly, the first electrode 200 includes a transparent conductive substrate 202 and a porous $TiO_2$ thin film 204. The porous $TiO_2$ thin film 204 carries the ruthenium complex prepared in Step (S2) as a dye-sensitizer. The second electrode 210 is similar to that mentioned in the previous embodiment, but the difference only lies in that the sealant 230 has two pores. The electrolyte fluid 220 is injected between the second electrode 210 and the first electrode 200 via one of the pores.
4. Finally, the pores of the sealant were sealed by a vacuum plastic (produced by Varian), so as to complete the fabrication of the closed cell.

In view of above, the present invention first provides a novel easily-synthesized heterocyclic tridentate system as a donor ligand system, and such ligand can also be used to prepare a ruthenium complex to serve as a dye-sensitizer, so as to effectively control the HOMO energy level, and thus reducing the band gap and promoting the metal-to-ligand charge transfer (MLCT) effect, thereby enhancing the charge separation efficiency. Furthermore, the scope for the dye sensitization is extended towards long wavelength, and the absorption region for the solar spectrum is increased. Meanwhile, the ruthenium complex of the present invention can be used as a photosensitive dye, which is suitable for fabricating solar cell devices with simple process, low price, and high efficiency. Furthermore, the solar cell device of the present invention can be easily fabricated into a large-area device, which has the advantages of being light and flexible, and having an environment-protective fabricating process.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A ruthenium complex represented by Formula (I) of RuL₁L₂X:

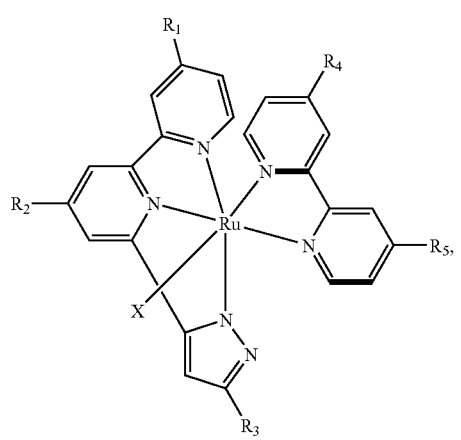

(I)

wherein L₁ represents a heterocyclic tridentate ligand with a structural formula (II):

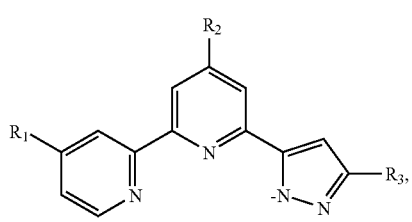

(II)

and L₂ represents a bipyridine ligand derivative with a structural formula (III):

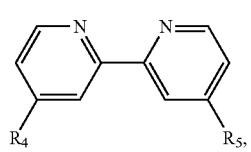

(III)

wherein $R_1$, $R_2$, $R_4$ and $R_5$ are the same or different substituents and represent alkyl, alkoxy, aminoalkyl, haloalkanes or substituted phenyl group, carboxylic acid group or acid radical salt thereof, sulfonic acid group or acid radical salt thereof, phosphoric acid group or acid radical salt thereof or hydrogen atom;

$R_3$ represents perhalogenated alkyl group, alkoxy, alkyl, amino, halogens, or hydrogen atom; and X is a monodentate anion ligand.

2. The ruthenium complex as claimed in claim 1, wherein $R_1$ of $L_1$ represents hydrogen or alkyl.

3. The ruthenium complex as claimed in claim 1, wherein $R_2$ of $L_1$ represents hydrogen or alkyl.

4. The ruthenium complex as claimed in claim 1, wherein $R_3$ of $L_1$ represents alkyl, perfluorinated alkyl, alkoxy or $CF_3$.

5. The ruthenium complex as claimed in claim 1, wherein $R_1$ of $L_1$ represents COOH or acid radical salt thereof.

6. The ruthenium complex as claimed in claim 1, wherein $R_2$ of $L_1$ represents COOH or acid radical salt thereof.

7. The ruthenium complex as claimed in claim 1, wherein $L_1$ has a structural formula (IV):

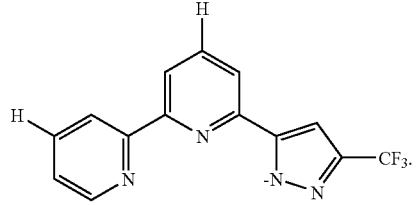

(IV)

8. The ruthenium complex as claimed in claim 1, wherein $R_1$ and $R_2$ of $L_1$ represent carboxylic acid group or acid radical salt thereof, and $R_3$ represents $CF_3$.

9. The ruthenium complex as claimed in claim 1, wherein X is halogens, halogen ions, halogen cyanide ions, sulfur cyanide ion, sulfite ion, or thiosulfate.

10. The ruthenium complex as claimed in claim 1, wherein $L_2$ represents 2,2'-bipyridine.

11. The ruthenium complex as claimed in claim 1, wherein $R_4$ and $R_5$ of $L_2$ represent carboxylic acid group or acid radical salt thereof, sulfonic acid group or acid radical salt thereof, phosphoric acid group or acid radical salt thereof.

12. The ruthenium complex as claimed in claim 1, wherein $L_2$ has a structural formula (V):

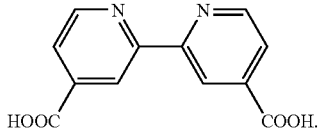

(V)

13. A dye-sensitized solar cell device, at least comprising:
a first electrode, comprising:
a transparent conductive substrate; and
a porous $TiO_2$ thin film, formed on a surface of the transparent conductive substrate, for carrying a dye-sensitizer thereon, wherein the dye-sensitizer is a ruthenium complex represented by Formula (I) of RuL₁L₂X:

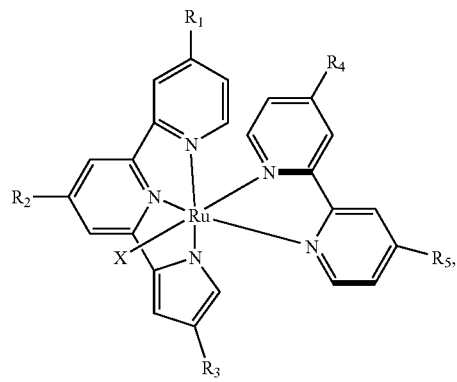

(I)

wherein L₁ is a heterocyclic tridentate ligand having a structural formula (II):

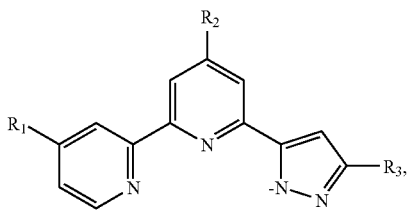

(II)

L₂ is a bipyridine ligand derivative having a structural formula (III):

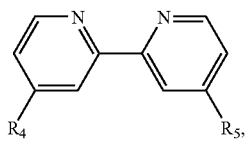

(III)

$R_1$, $R_2$, $R_4$ and $R_5$ are the same or different substituents and represent alkyl, alkoxy, aminoalkyl, haloalkanes or substituted phenyl group, carboxylic acid group or acid radical salt thereof, sulfonic acid group or acid radical salt thereof, phosphoric acid group or acid radical salt thereof or hydrogen atom;

$R_3$ represents perhalogenated alkyl group, alkoxy, alkyl, amino, halogens, or hydrogen atom; and X is a monodentate anion ligand;

a second electrode; and an electrolyte fluid, located between the surface of the transparent conductive substrate and the second electrode.

14. The dye-sensitized solar cell device as claimed in claim 13, wherein $R_1$ of $L_1$ represents hydrogen or alkyl.

15. The dye-sensitized solar cell device as claimed in claim 13, wherein $R_2$ of $L_1$ represents hydrogen or alkyl.

16. The dye-sensitized solar cell device as claimed in claim 13, wherein $R_3$ of $L_1$ represents alkyl, perfluorinated alkyl group, alkoxy or $CF_3$.

17. The dye-sensitized solar cell device as claimed in claim 13, wherein $R_1$ and $R_2$ of $L_1$ represents COOH or acid radical salt thereof.

18. The dye-sensitized solar cell device as claimed in claim 13, wherein $L_1$ has a structural formula (IV):

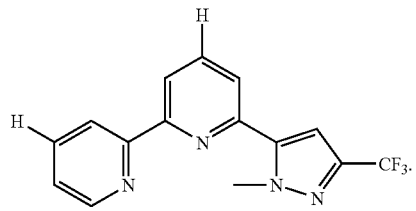

(IV)

19. The dye-sensitized solar cell device as claimed in claim 13, wherein X is halogen, halogen ions, halogen cyanide ions, sulfur cyanide ion, sulfite ion, or thiosulfate.

20. The dye-sensitized solar cell device as claimed in claim 13, wherein $L_2$ represents 2, 2'-bipyridine.

21. The dye-sensitized solar cell device as claimed in claim 13, wherein $R_4$ and $R_5$ of $L_2$ represent carboxylic acid group or acid radical salt thereof, sulfonic acid group or acid radical salt thereof, phosphoric acid group or acid radical salt thereof.

* * * * *